(12) United States Patent
Gannoe et al.

(10) Patent No.: US 9,119,613 B2
(45) Date of Patent: Sep. 1, 2015

(54) SYSTEM AND METHOD FOR TRAPEZIUM BONE REPLACEMENT

(75) Inventors: Jamy Gannoe, West Milford, NJ (US); Luis A. Arellano, Fair Lawn, NJ (US)

(73) Assignee: Extremity Medical LLC, Parsippany, NJ (US)

( * ) Notice: Subject to any disclaimer, the term of this patent is extended or adjusted under 35 U.S.C. 154(b) by 1108 days.

(21) Appl. No.: 12/319,438

(22) Filed: Jan. 7, 2009

(65) Prior Publication Data

US 2009/0254190 A1  Oct. 8, 2009

Related U.S. Application Data

(60) Provisional application No. 61/010,301, filed on Jan. 7, 2008.

(51) Int. Cl.
| | |
|---|---|
| A61F 2/42 | (2006.01) |
| A61B 17/04 | (2006.01) |
| A61F 2/46 | (2006.01) |
| A61F 2/30 | (2006.01) |
| A61B 17/80 | (2006.01) |
| A61B 17/84 | (2006.01) |

(52) U.S. Cl.
CPC ........... *A61B 17/0401* (2013.01); *A61F 2/4261* (2013.01); *A61F 2/4606* (2013.01); *A61F 2/4684* (2013.01); *A61B 17/8061* (2013.01); *A61B 17/842* (2013.01); *A61B 2017/044* (2013.01); *A61B 2017/0414* (2013.01); *A61F 2002/3092* (2013.01); *A61F 2002/30464* (2013.01); *A61F 2002/30588* (2013.01); *A61F 2002/30772* (2013.01); *A61F 2002/4258* (2013.01); *A61F 2002/4276* (2013.01)

(58) Field of Classification Search
CPC ................ A61F 2002/4258; A61F 2002/4276; A61F 2002/30464
USPC ............................................ 623/21.11–21.14
See application file for complete search history.

(56) References Cited

U.S. PATENT DOCUMENTS

| | | | | |
|---|---|---|---|---|
| 3,924,276 | A | * | 12/1975 | Eaton ......................... 623/21.15 |
| 4,198,712 | A | | 4/1980 | Swanson |
| 5,702,470 | A | | 12/1997 | Menon |
| 5,888,203 | A | | 3/1999 | Goldberg |
| 6,017,366 | A | | 1/2000 | Berman |
| D450,121 | S | | 11/2001 | Anderson |
| D472,633 | S | | 4/2003 | Anderson |
| D493,225 | S | | 7/2004 | Varga et al. |
| 7,182,787 | B2 | | 2/2007 | Hassler et al. |
| 2005/0251265 | A1 | | 11/2005 | Calandruccio et al. |
| 2006/0241777 | A1 | * | 10/2006 | Partin et al. ................ 623/21.11 |
| 2007/0021839 | A1 | | 1/2007 | Lowe |
| 2008/0269908 | A1 | | 10/2008 | Warburton |

OTHER PUBLICATIONS

Gray, Henry. Anatomy of the Human Body. Philadelphia: Lea & Febiger, 1918; Bartleby.com, 2000. www.bartlby.com/107, printed Mar. 17, 2015.*

* cited by examiner

*Primary Examiner* — Yashita Sharma
*Assistant Examiner* — Megan Wolf
(74) *Attorney, Agent, or Firm* — Ward & Zinna, LLC

(57) ABSTRACT

A carpometacarpal joint replacement system for replacing the trapezium bone in the hand is provided. The system includes a trapezial implant for the carpometacarpal joint resulting in replacement of the carpal trapezium bone with a prosthesis having the same anatomical configuration as the trapezium bone. The implant device comprises a plurality of concave surfaces, with the plurality of concave surfaces articulating with the carpal and metacarpal bones.

20 Claims, 21 Drawing Sheets

SYSTEM AND METHOD FOR TRAPEZIUM BONE REPLACEMENT

CROSS-REFERENCE TO RELATED APPLICATIONS

This invention claims the benefit of U.S. Provisional Application No. 61/010,3013, filed Jan. 7, 2008, which is incorporated herein by reference.

FIELD OF THE INVENTION

This invention relates to the field of orthopedic implant devices, and more particularly, to a system and method for trapezium bone replacement at the carpometacarpal joint utilizing a trapezial implant.

BACKGROUND OF THE INVENTION

Conditions such as osteoarthritis, deformity, cancer or trauma may cause degeneration of the articular surfaces between the trapezium and the first metacarpal as well as the other carpal and metacarpal bones in a hand. This causes the patient discomfort, severe pain, aseptic necrosis, and/or arthritis of the carpal bones. Surgical treatment of these conditions have included intercarpal fusion, arthroplasty, wrist fusion, local resection, proximal row carpectomy, bone grafting, radial styloidectomy, radial shortening or ulnar lengthening, and interposition arthroplasty. Among these processes, fusion procedures are not generally preferred. Although pain may be relieved, the stability, power and mobility of the joint are affected. Local resection procedures involving the removal of an irreversibly pathological bone result in instability and migration of adjacent carpal bones into the space left after the resection. This migration causes in instability in the wrist joint. In addition, metallic and ceramic implants developed for replacement of carpal bones have not been satisfactory due to problems relating primarily to, migration of the implant, implant loosening and absorption of bone due to hardness of the material inserted and poor force distribution.

Arthritis is one of the most prevalent causes of adult impairment affecting the small joints of the hand and wrist. Disability results from the grinding of adjacent bones whose natural articular surfaces are stripped of slippery cartilage and become rough from disease. One form of the disease is particularly prevalent and debilitating. It causes the osteoarthritic degeneration of the thumb basal joint (which is also known as carpometacarpal (CMC) joint), and affects as many as half of all post-menopausal women. The CMC joint is where the saddle-shaped trapezium bone articulates with the first metacarpal bone allowing motion like that of a mechanical universal joint. An arthritic CMC joint becomes painful enough to limit everyday activity such as grasping or pinching. Symptoms can often be treated with physical therapy, rest, splinting or anti-inflammatory medication. If pain persists, surgery may be indicated to allow return to activities of normal daily living.

Interposition arthroplasty, the most commonly performed surgical procedure for treating CMC arthritis, has been in use since the early 1970's. Interposition arthroplasty is a procedure where a biologic or synthetic material is interposed between the bones once the degenerated joint surfaces are removed. The interpositional material serves as a short term cushion to prevent bone to bone contact and to provide a scaffold for heeling into a surgically created void.

Known surgical intervention for treatment of CMC arthritis begins with the removal of the diseased tissue. Usually the entire trapezium bone or a portion thereof is removed. To prevent the collapse of the first metacarpal bone into the space thus created, a wire pin is often used to align the base of the first metacarpal bone with the base of the index metacarpal. The pin serves as a temporary stabilizer. A tendon, such as the palmaris longus or flexor carpi radialis is harvested from the forearm and rolled up, resembling a rolled "anchovy" or jelly-roll. The anchovy is then sutured to prevent unrolling and is interposed between the base of the thumb metacarpal and the scaphoid (the space previously occupied by the trapezium bone). In some cases, a suspensionplasty is performed wherein a further piece of tendon is used to tie the base of the thumb metacarpal to the base of the index metacarpal, thereby "suspending" the thumb metacarpal. The wire pin is left in place for about 4 to 6 weeks while healing occurs. It is usually 8 weeks or more before patients are allowed unrestricted activity.

Although the results of tendon interposition may be acceptable, there are a number of drawbacks to this procedure. As with any procedure requiring the use of a graft, there is additional surgical trauma and morbidity associated with the graft donor site. In many circumstances, there is not enough tendon available from which a graft may be harvested or the quality of the tissue is inadequate. Another major drawback is the amount of time it takes to harvest a tendon graft and prepare it for interpositional placement. Adding a suspensionplasty can also significantly increase operating time. There is evidence that during healing, the tendon grafts weaken and lose structural strength. Thus, the use of pins becomes necessary to help hold the thumb metacarpal in the right position until dense scar tissue forms that will ultimately support the metacarpal. Also, evidence shows that over the long term, thumb shortening and other anatomical changes may occur which have a deleterious effect on joint function and strength.

Prosthetic material has also been used to treat CMC arthritis. One widely used material has been silicone rubber. Several implant designs have been manufactured from these materials, including a cylindrical spacer with a long stem fitted into a canal formed into the metacarpal. Another design of silicone rubber implant comprises a button-shaped spacer with a small locating pin. Problems with fracture and dislocation of the aforementioned implants led to the development of other designs that incorporated a polyethylene terephthalate or polytetrafluoroethylene fabric mesh in order to improve strength and to allow tissue ingrowth for fixation to the metacarpal. Another implant contains a perforation to allow fixation by attaching a slip of the flexor carpi radialis tendon. However, all of these silicone rubber devices were subject to dislocation, fracture, abrasion and fatigue that led to the generation of small particles of silicone. The term "silicone synovitis" was coined to describe the chronic inflammatory reaction that resulted from this liberation of silicone particles.

There have been many attempts to address the problems associated with hard implants and degradation of silicone implants by designing two piece implants that were intended to reconstruct an articulating joint. Many of the early designs were basically a ball and socket joint on simple stems that require taking out or shaping multiple bones causing the surgery to be more complicated and invasive.

None of the described prosthetic interposition arthroplasty and CMC joint reconstruction devices have met with an acceptable degree of success. Problems are mostly associated with long-term breakdown, loosening, or dislocation. For these reasons tendon interposition with or without suspensionplasty has been used even despite the inherent problems associated with tissue graft harvesting, protracted operating room time and long term biomechanics, strength, function and deformity issues.

There is therefore a need for a trapezium bone implant for the carpometacarpal joint resurfacing implant, system and method of use that overcomes some or all of the previously delineated drawbacks of prior carpometarcarpal joint resurfacing implants.

SUMMARY OF THE INVENTION

An object of the invention is to overcome the drawbacks of previous inventions.

Another object of the invention is to provide a novel and useful system for replacing the trapezium bone in the carpometacarpal joint.

Another object of the invention is to provide a anatomically correct trapezial implant device that makes direct contact with native bone and cartilage in an anatomically correct manner to more effectively distribute forces Another object of the invention is to provide a trapezial implant device that allows for implant stability within the carpometacarpal (CMC) joint.

In a first non-limiting aspect of the invention, a prosthetic device for replacing a trapezium in a human hand is provided and comprises a rigid body having a first articulating surface for engaging a proximal surface of a first metacarpal in the hand and a second articulating surface for engaging a distal surface of a scaphoid bone in the hand. The prosthetic device also includes a through-aperture longitudinally formed in the body with the through-aperture being tapered at an angle from an ulnar face to a radial face. The through-aperture is also formed to receive sutures and/or straps/tapes to promote attachment and adhesion of surrounding ligaments to the body after placement of the prosthetic device.

In a second non-limiting aspect of the invention, a trapezium replacement system is provided comprising a body having a first articulating surface for engaging a proximal surface of a first metacarpal in the hand and a second articulating surface for engaging a distal surface of a scaphoid bone in said hand. The body has an aperture longitudinally formed in the body, with the aperture being tapered at an angle from an ulnar face to a radial face. The trapezium replacement system also includes a threaded screw member being received in the aperture. The threaded screw member has a leading end and a trailing end. The threaded screw member further comprises a strap coupled to the trailing end. The system also comprises a holder instrument for engaging the body. The holder instrument includes a handle portion having a first end and an opposed second end, a rod portion coupled to the handle portion at said second end, a tubular portion for receiving the rod portion and a tip portion coupled to the rod portion for controlling engagement of the holder instrument with the body.

In a third non-limiting aspect of the invention, a method treating the carpometacarpal joint and comprises ten steps. In step one, the trapezium bone from a hand of a human is excised to create a trapezial cavity. In step two, a trial inserter is utilized to select a correct-sized trapezial implant device. The trapezial implant device is sized and shaped to resemble the excised trapezium bone. In step three, a hole is drilled in the second metacarpal bone to a preferred depth and location. In step four, a strap is into the hole of the second metacarpal. In step five, the strap is secured to the second metacarpal with an interference screw. In step six, the loose end of the strap is inserted into the trapezial implant device from an ulnar face of the device to a radial face of the device. In step seven, a second hole is drilled in the first metacarpal bone to a preferred depth and location. In step eight, the strap is placed under tension. In step nine, the strap is inserted into the second hole in the first metacarpal and secured with interference screws. In step ten, the tails of the strap are attached to the trapezial implant device to promote attachment and adhesion of the trapezial implant device.

BRIEF DESCRIPTION OF THE DRAWINGS

A further understanding of the invention can be obtained by reference to a preferred embodiment set forth in the illustrations of the accompanying drawings. Although the illustrated embodiment is merely exemplary of systems and methods for carrying out the invention, both the organization and method of operation of the invention, in general, together with further objectives and advantages thereof, may be more easily understood by reference to the drawings and the following description. The drawings are not intended to limit the scope of this invention, which is set forth with particularity in the claims as appended or as subsequently amended, but merely to clarify and exemplify the invention.

For a more complete understanding of the invention, reference is now made to the following drawings in which.

DETAILED DESCRIPTION OF THE INVENTION

The invention may be understood more readily by reference to the following detailed description of the preferred embodiment of the invention. However, techniques, systems and operating structures in accordance with the invention may be embodied in a wide variety of forms and modes, some of which may be quite different from those in the disclosed embodiment. Consequently, the specific structural and functional details disclosed herein are merely representative. Yet in that regard, they are deemed to afford the best embodiment for purposes of disclosure and to provide a basis for the claims herein, which define the scope of the invention. It must be noted that, as used in the specification and the appended claims, the singular forms "a", "an", and "the" include plural referents unless the context clearly indicates otherwise.

The trapezial implant device is designed to replace the carpal trapezium bone and has the same anatomical configuration of the trapezium bone. The trapezial implant device is designed to fit within the cavity created by the excision of the carpal trapezium (i.e., a trapeziectomy) and is designed as an articular spacer with deep concavities to receive and secure the head of the first metacarpal, and possibly also the second metacarpal, the trapezoid and the scaphoid. As such, the trapezial implant device maintains the relationship with the adjacent trapezoid, first metacarpal, second metacarpal and scaphoid bones. Further, the trapezial implant device is intended for use in cases of isolated carpometacarpal (CMC) joint movement from either degenerative arthritis or post-traumatic arthritis presenting decreased motion, X-ray evidence of arthritic changes or subluxation of the carpometacarpal joint, localized pain and palpable crepitation during circumduction movement with axial compression of the involved thumb, associated unstable, stiff, or painful distal joints, or decreased pinch and grip strength. As the trapezial implant device has the same anatomical configuration of the trapezium, it distributes the forces more effectively to reduce stresses on bony structures, improve strength and function and minimize onset of post operative deformity.

Figure 1:
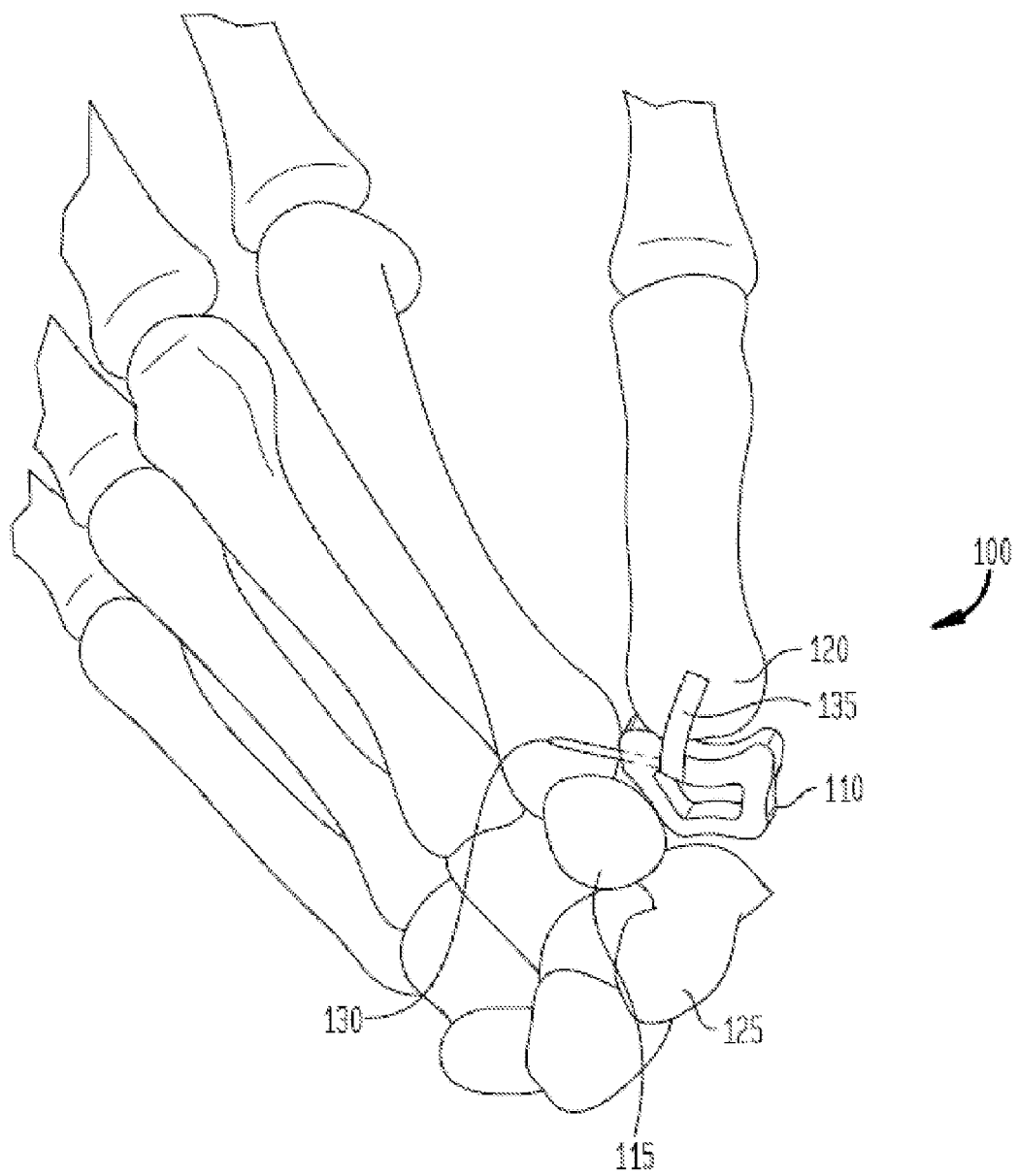
FIG. 1 is a perspective view of a hand with a trapezial implant device according with a preferred embodiment of the invention.

Referring now to FIG. 1, there is shown a carpometacarpal (CMC) joint replacement system 100 in accordance with the teachings of the preferred embodiment of the invention. As shown, CMC joint replacement system 100 includes trapezial implant device 110, which resides in the cavity created by selectively removing the trapezium (not shown). Trapezial implant device 110 has a plurality of saddle-shaped concavities on its surface in order to articulate with the adjacent trapezoid 115, first metacarpal 120 and scaphoid 125 bones as well as a convex surface to articulate with the second metacarpal 130. The CMC joint replacement system 100 includes, in one non-limiting example, straps, such as strap 135 to increase stability of the trapezial implant device 110. It should be appreciated that in one non-limiting embodiment, trapezial implant device 110 may be made from Titanium, although, in other non-limiting embodiments, trapezial implant device 110 may be made from Stainless Steel (SST), Polyetheretherketone (PEEK), Cobalt Chrome, polyethylene, polymer, elastomer, silicone, polycarbonate, polyurethane or other similar types of biocompatible materials.

Figure 2:
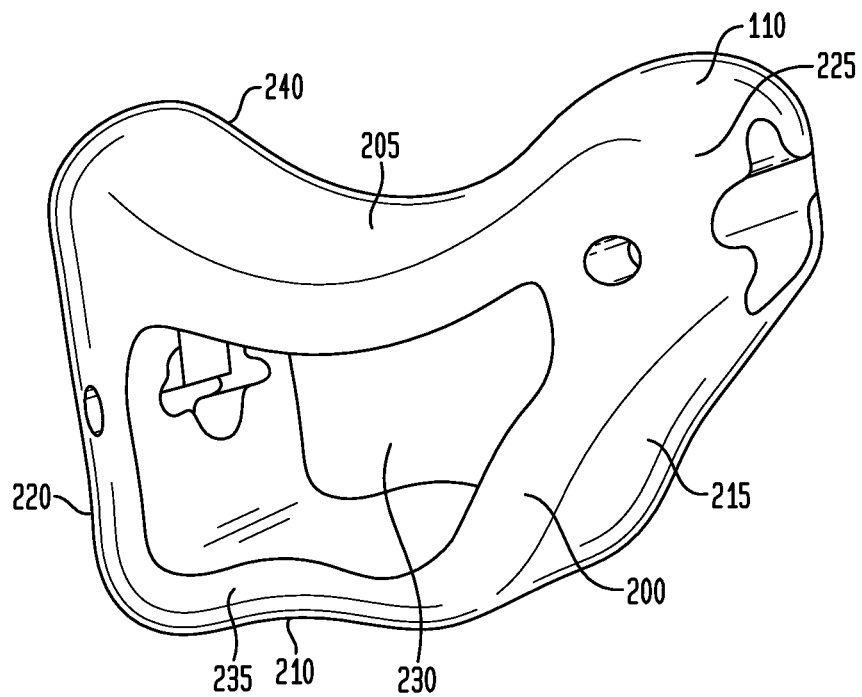
FIG. 2 is a perspective view of the trapezial implant device used in the carpometacarpal joint replacement system in accordance with the preferred embodiment of the invention.

As shown in FIG. 2, trapezial implant device 110 preferably has a rigid body 200 and comprises an anatomically correct shape that conforms to the shape of a trapezium bone. Trapezial implant device 110 has a plurality of concave articulating surfaces where rigid body 200 makes contact with the adjacent bones in the hand (not shown). Particularly, trapezial implant device 110 preferably has a first concave surface 205 to articulate with the adjacent proximal surface of the first metacarpal bone 120 (shown previously in FIG. 1) and a second concave surface 210 to articulate with the articulating surface of the distal scaphoid bone 125 (shown previously in FIG. 1). Also, trapezial implant device 110 has a third concave surface 215 to articulate with the radial articulating surface of the trapezoid bone 115 (shown previously in FIG. 1), a radial face 220 and an opposed ulnar face 225 to articulate with the second metacarpal bone 130 of the hand (shown previously in FIG. 1).

Through hole 230 traverses rigid body 200 from dorsal face 235 to volar face 240, and provides an opening in order to couple trapezial implant device 110 to the body via bridging tissue formation, such as in hematoma distraction arthroplasty or encapsulation. It should be appreciated that the dimension of through hole 230 may vary based on the preferences of a surgeon or a manufacturer. It should also be appreciated that surfaces 205, 210, 215, and 225 which articulate with adjacent bones, make direct contact with native bone and cartilage and aid and promote the stability of trapezial implant device 110 within the carpometacarpal joint. In other non-limiting embodiments, inner walls and non-articulating faces of the trapezial implant device 110 may be coated with media, for example, porous beads, that promote soft tissue in-growth, on-growth and through-growth, and which further promotes trapezial implant device 110 stability.

Figure 3:
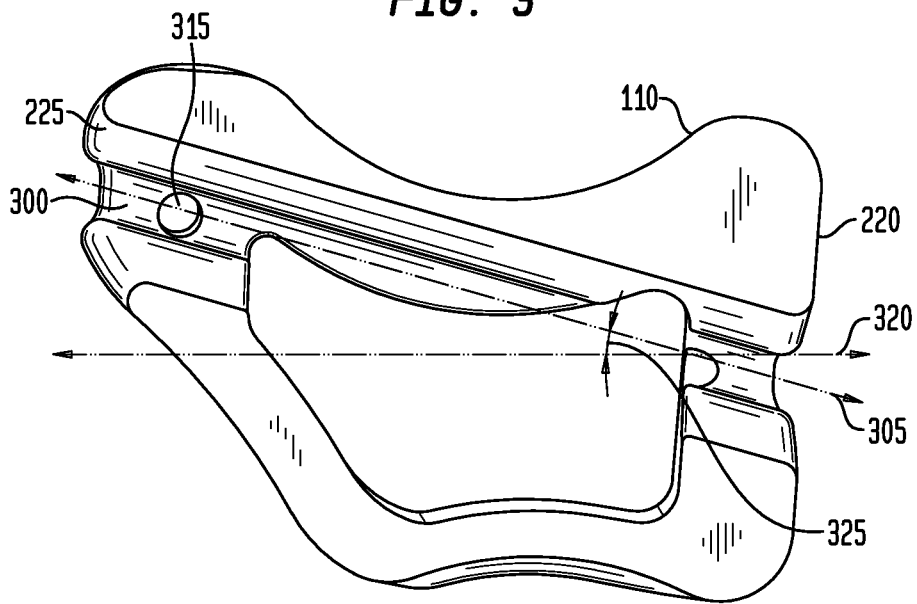
FIG. 3 is a cross-sectional view of the trapezial implant device used in the carpometacarpal joint replacement system shown in FIG. 2 according to the preferred embodiment of the invention.

As shown in FIG. 3, trapezial implant device 110 contains a through hole or aperture 300 forming a continuous opening from ulnar face 225 to radial face 220. Aperture 300 is tapered along axis 305 (i.e., aperture 300 forms an angle 325 with horizontal axis 320 and provides a trajectory for receiving a fixation or anchoring device for sutures, straps, staples, tapes or the like. Trapezial implant device 110 is also provided with one or more holes, such as hole 315, at the corners of trapezial implant device 110 to allow for weaving and attaching sutures, straps, tapes or the like to increase the stability of the trapezial implant device 110 with respect to the adjacent bones in the hand.

Figure 4:
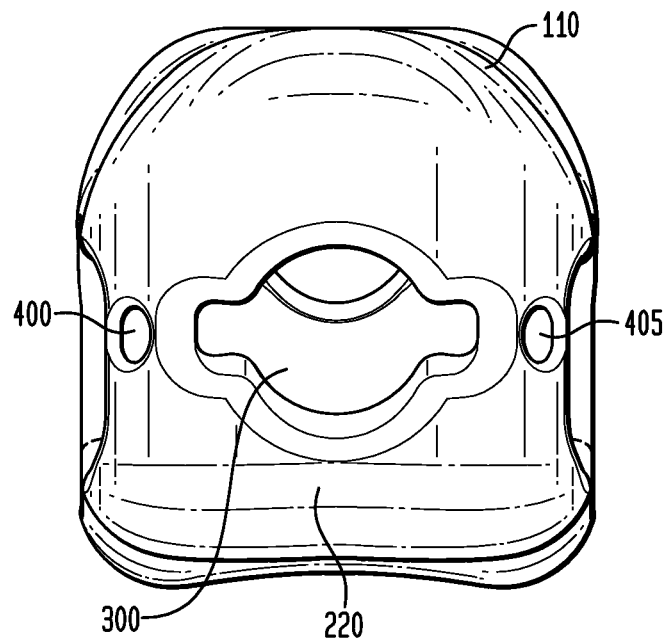
FIG. 4 is a view of the radial face of the trapezial implant device shown in FIG. 2 according to the preferred embodiment of the invention.

As shown in FIG. 4, trapezial implant device 110 is provided with through hole 300 on radial face 220 as well as one or more substantially similar holes 400 and 405 on the radial face 220. Holes 400 and 405 are provided to receive sutures, staples or the like, in order to attach trapezial implant device 110 to adjacent bones, ligaments or other tissue, thereby increasing the stability of trapezial implant device 110 in the hand (not shown).

Figure 5:
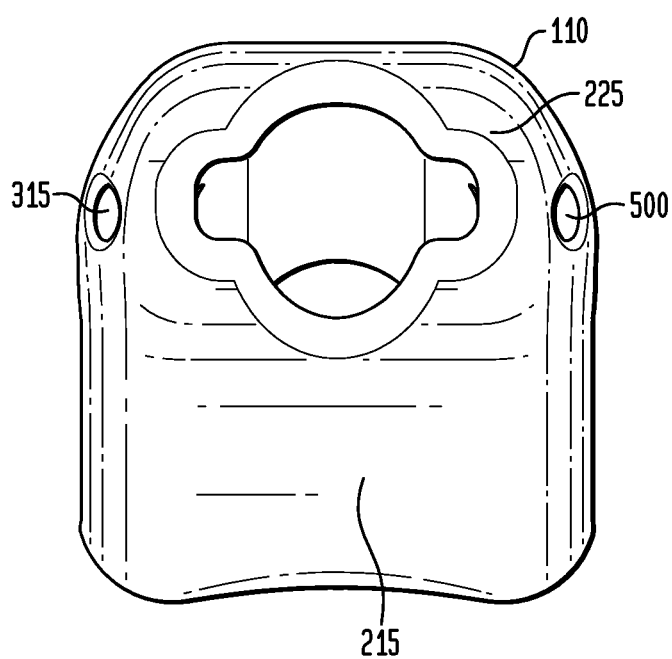
FIG. 5 is a view of the ulnar face of the trapezial implant device shown in FIG. 2 according to the preferred embodiment of the invention.

As shown in FIG. 5, trapezial implant device 110 contains the concave surface 215 provided to articulate with the radial articulating surface of the trapezoid bone (not shown) and the ulnar face 225 to articulate with the second metacarpal bone of the hand. Concave surface 215 and ulnar face 225 each make direct contact with native bone and cartilage, which aid and promote the stability of trapezial implant device 110 within the carpometacarpal joint. Also, the plurality of holes 315 and 500 are provided to allow for weaving and attachment points for sutures, staples or the like to increase the stability of trapezial implant device 110.

Figure 6:
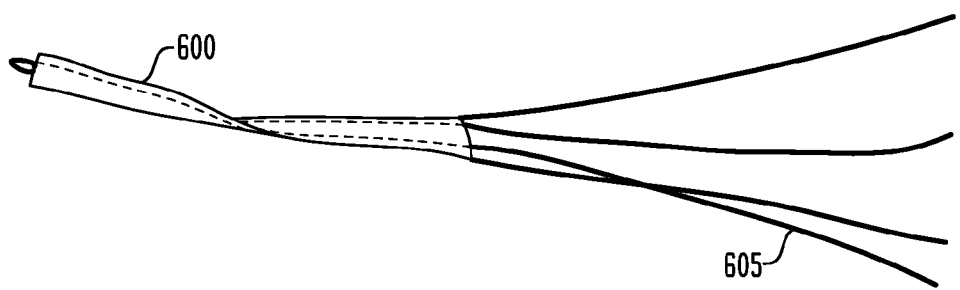
FIG. 6 is a perspective view of the straps used in the carpometacarpal joint replacement system according to the preferred embodiment of the invention.

FIG. 6 illustrates, in one non-limiting embodiment, a strap 600 utilized with trapezial implant device 110 (not shown) in order to attach trapezial implant device 110 to adjacent bones and ligaments. In other non-limiting embodiments, a suture, a staple, a ribbon or other similar type of materials may be utilized with trapezial implant device 110. Strap 600 is generally ribbon-shaped and includes ribbon-tails 605 to allow for weaving the ribbon-tails 605 through the plurality of holes 400, 405 (shown in FIG. 4) and 315 and 500 (shown in FIG. 5) as well as to adjacent bones and/or ligaments thereby increasing the stability of the trapezial implant device 110 in the carpometacarpal joint.

Figure 7:
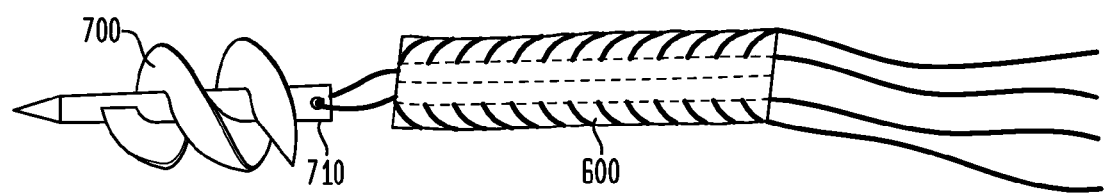
FIG. 7 is a perspective view of the strap shown in FIG. 6 attached to a threaded screw anchor used in the carpometacarpal joint replacement system according to an embodiment of the invention.

As shown in FIG. 7, strap 600 is coupled to a cancellous threaded screw anchor 700 at trailing end 710. Threaded screw anchor 700 is utilized to insert strap 600 through trapezial implant device 110 and into adjacent bone, such as second metacarpal in order to anchor threaded screw anchor 700 into second metacarpal bone and couple trapezial implant device 110 to second metacarpal bone (as later shown and described with reference to FIGS. 14 through 16). In other non-limiting embodiments, a cortical threaded screw or a semi-cancellous, semi-cortical threaded screw may be utilized to insert strap 600 into adjacent bone. Strap 600 is preferably made of polyester, although, in other non-limiting embodiments, strap 600 may be made of polypropylene, EPTFE, polyethylene, or any other similar types of materials.

Figure 8:
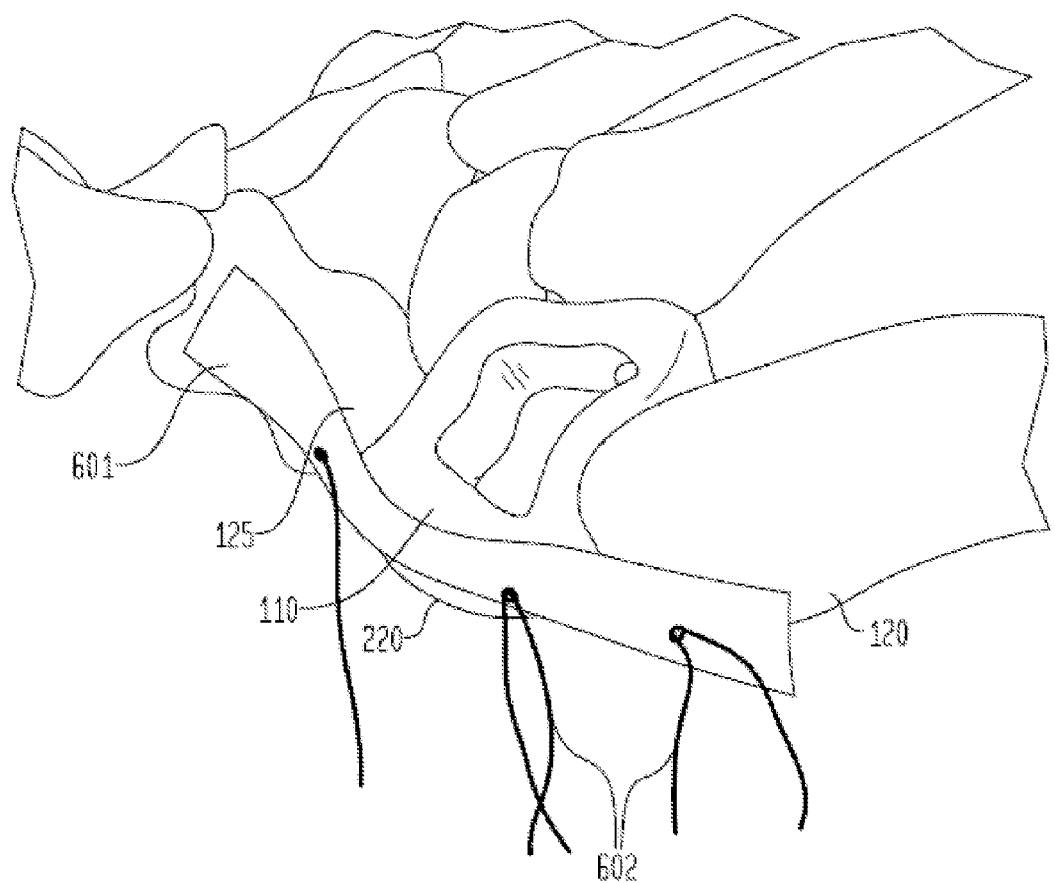
FIG. 8 is a perspective view of a strap used in the carpometacarpal joint replacement system according to yet another embodiment of the invention.

FIG. 8 illustrates another non-limiting example of an attachment strap 601. Strap 601 attaches to the radial face 220 of trapezial implant device 110, anterior head of adjacent first metacarpal bone 120 and radial surface of the scaphoid 125 bones using strap tails 602 in order to increase trapezial implant device 110 stability. In other non-limiting embodiments, strap 601 and/or tails 602 may be attached to soft tissue to additionally increase stability of trapezial implant device 110.

Figure 9:
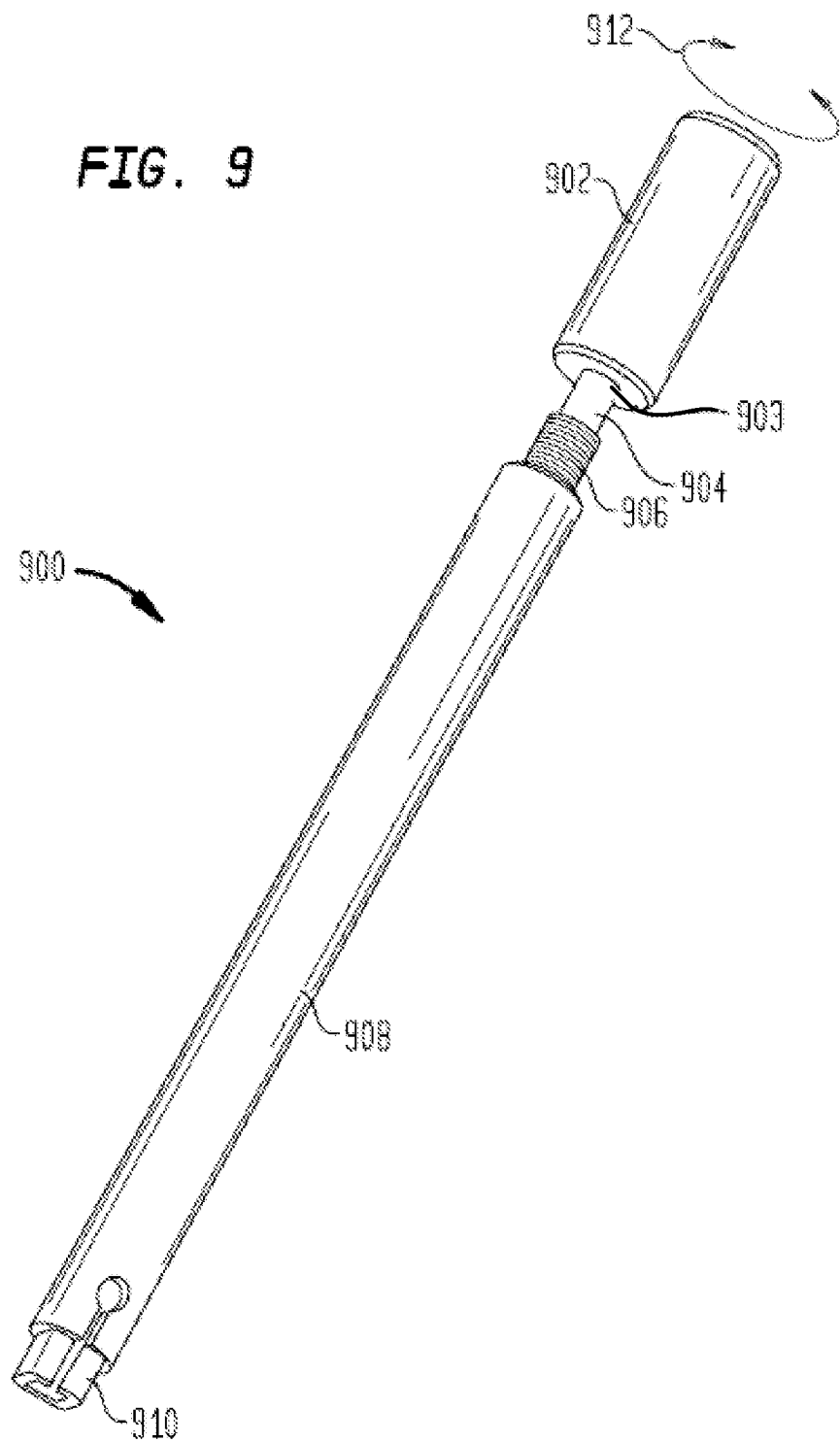
FIG. 9 is a perspective view of holder instrument used in the carpometacarpal joint replacement system according to the preferred embodiment of the invention.

Referring now to FIG. 9, holder instrument 900 is illustrated for inserting trapezial implant device 110 (not shown) during a carpometacarpal joint replacement procedure. Holder instrument 900 includes a generally cylindrical handle portion 902 coupled to a tubular rod portion 904. Rod portion 904 has a first end 903 fixedly coupled to handle portion 902 and a threaded second end 906, which partially resides within a generally tubular portion 908. Also, tubular portion 908 terminates into a "box-drive" tip portion 910. Tip portion 910 is provided to be received in aperture 300 at radial face 220 of trapezial implant device 110 (shown in FIG. 2). Tip portion 910 engages trapezial implant device 110 in a secure interference fit as handle portion 902 is rotated along arcuate axis 912. This rotation causes tip portion 910 to spread, thereby causing tip portion 910 to apply a frictional force within aperture 300 at radial face 220 (shown in FIG. 2). Similarly, tip portion 910 may be retracted from aperture 300 of trapezial implant device 110 by correspondingly rotating handle portion 902 along direction of arc 912, which causes the tip portion 910 to compress.

Figure 10:
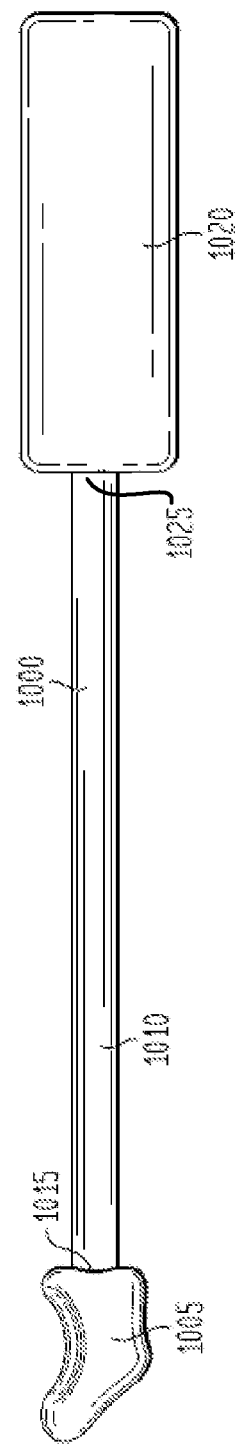
FIG. 10 is a perspective view of trial inserter device used in the carpometacarpal joint replacement system according to the preferred embodiment of the invention.

FIG. 10 illustrates a trial inserter device 1000 utilized by a surgeon for selecting an appropriate trapezial implant device 110 (previously shown in FIGS. 1-5) for performing a carpometacarpal joint replacement procedure. Particularly, trial inserter device 1000 includes a trial portion 1005 that is substantially similar to trapezial implant device 110 as was shown in FIGS. 1-5. Also, trial portion 1005 terminates into a rod portion 1010. Rod portion 1010 is generally cylindrical in shape and is coupled to trial portion 1005 at end 1015. Rod portion 1010 is also coupled to handle portion 1020 at end 1025. In operation, trial inserter device 1000 would be utilized to assist the surgeon in achieving the proper depth, positioning and alignment of trapezial implant device 110. Trial inserter device 1000 also would assist the surgeon in estimating the size of trapezial implant device 110 (previously shown in FIGS. 1-5) that is needed for carpometacarpal joint replacement.

Figure 11:
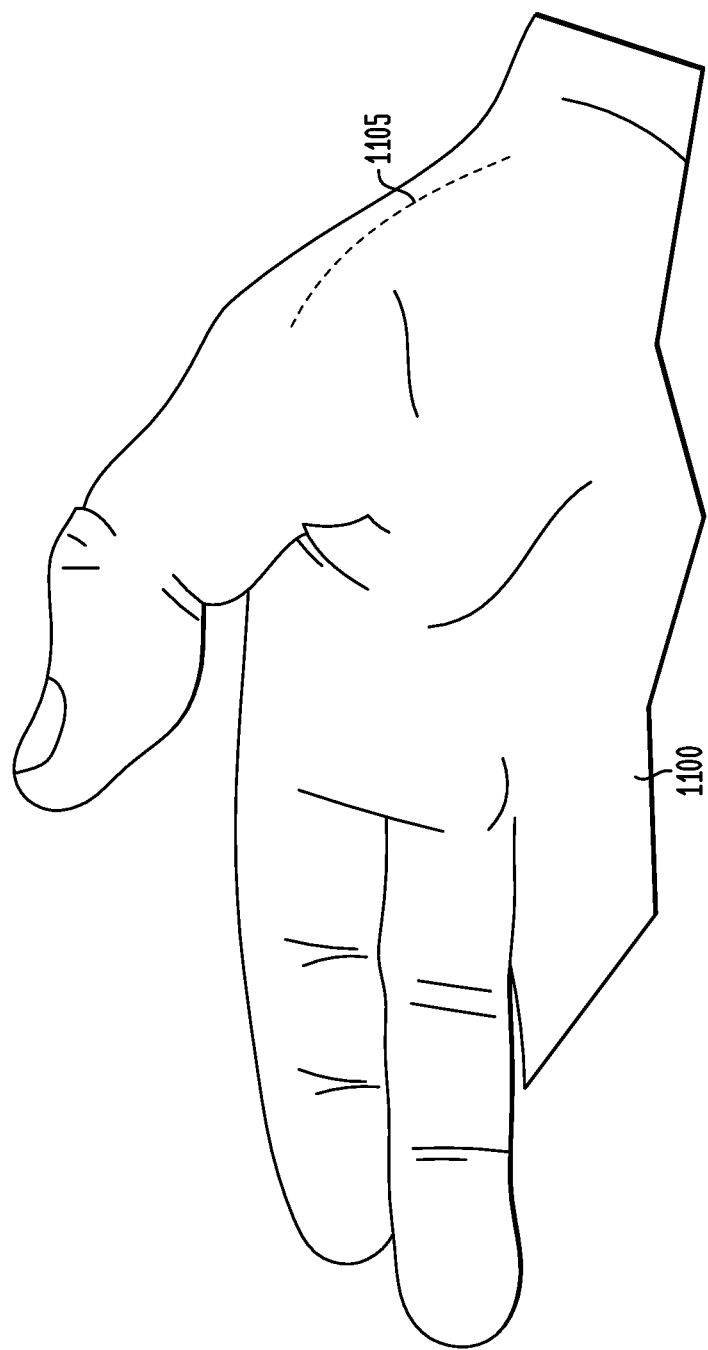
FIG. 11 illustrates the location of the incision in the carpometacarpal joint.

As shown in FIGS. 11-21, trapezial implant device 110, trial inserter device 1000 and strap 600 may be utilized to provide a carpometacarpal joint replacement system 100 and procedure to replace the carpal trapezium bone in a human hand 1100 (shown in FIG. 11). It should be appreciated that other instruments utilized for replacing the trapezium bone are commonly used instruments in surgical techniques that are readily available to a surgeon.

Figure 12:
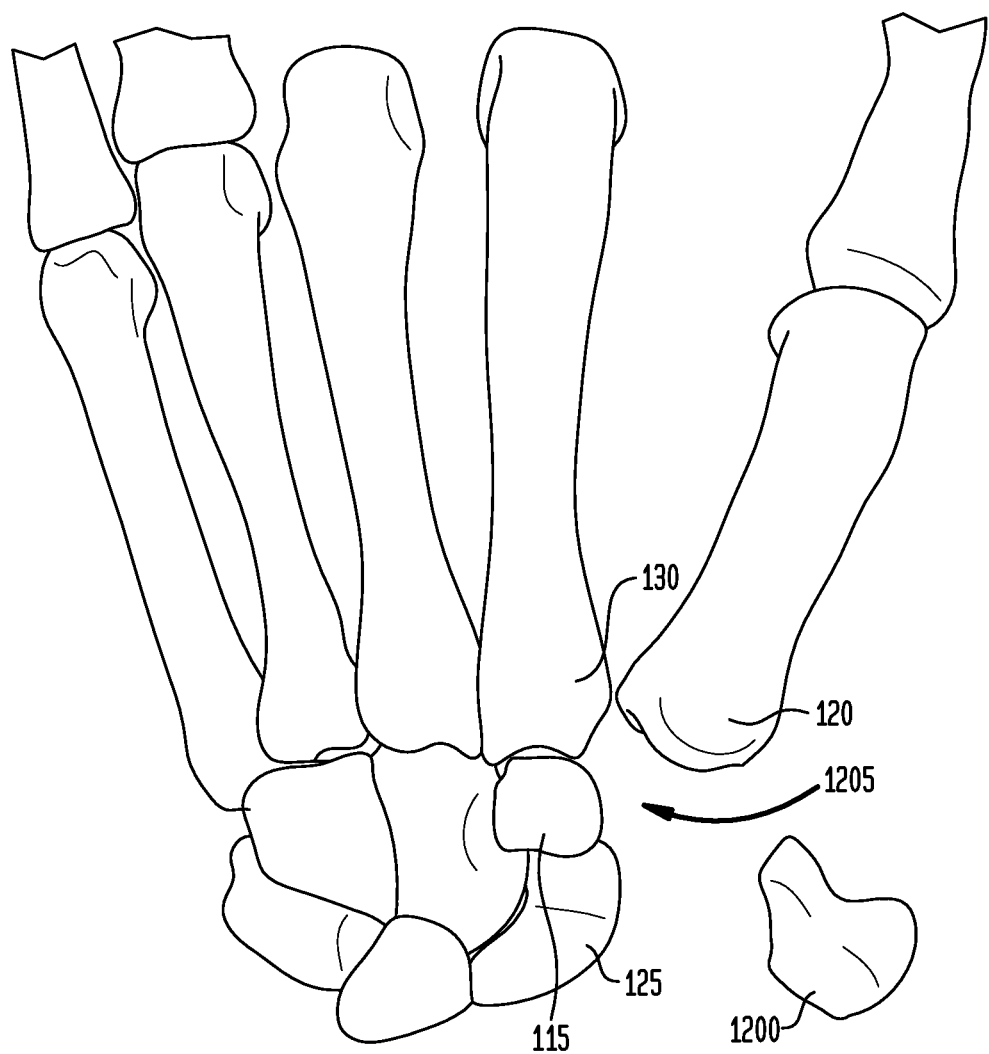
FIG. 12 illustrates a step of removing the trapezium according to the preferred embodiment of the invention.

Referring now to FIG. 11, incision 1105 is made about the dorsal-radial longitudinal base of the thumb carpometacarpal (CMC) joint of the human hand 1100. As shown in FIG. 12, the trapezium 1200 is removed (i.e., a trapeziectomy is performed) thereby forming a trapezial cavity 1205 between first metacarpal 120, scaphoid 125, second metacarpal 130 and trapezoid 115 bones.

Figure 13:
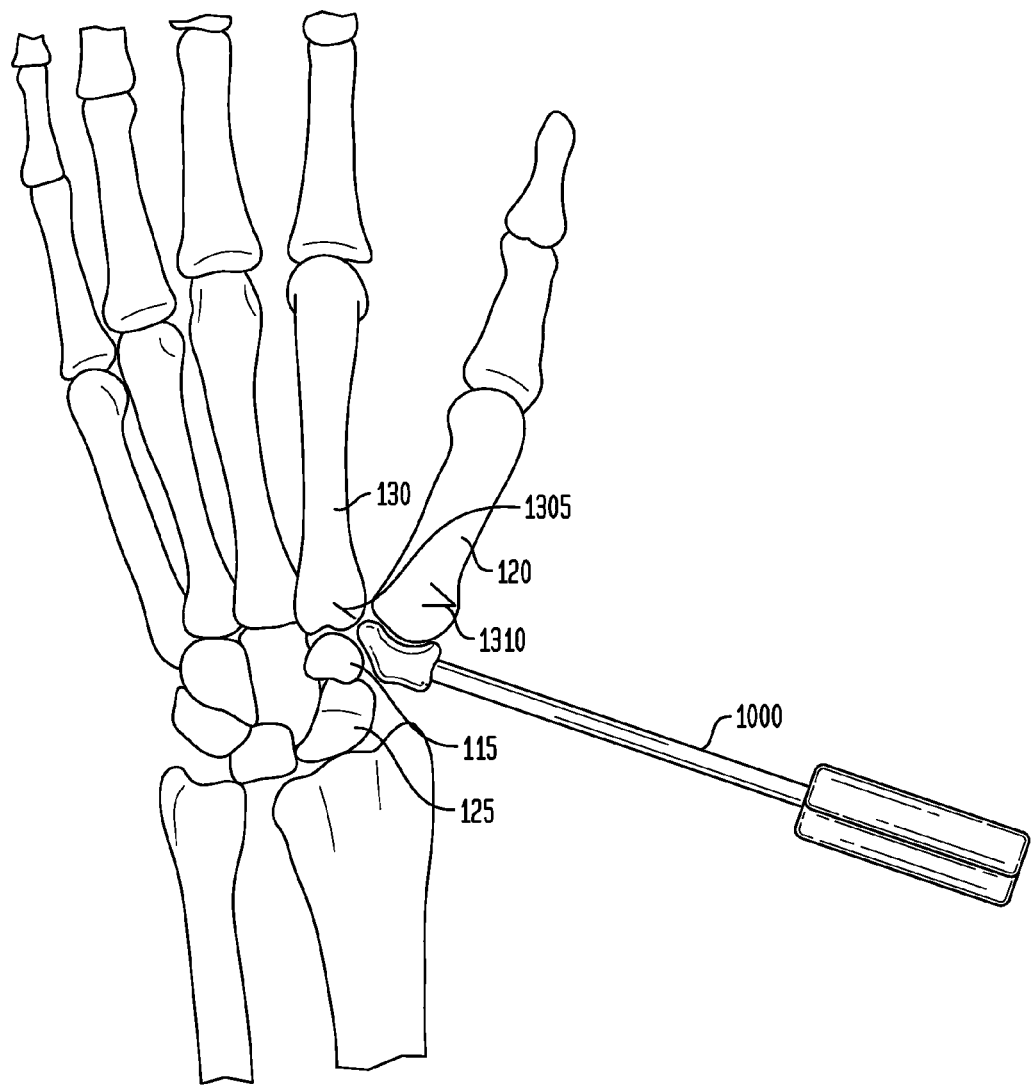
FIG. 13 illustrates a step of using the trial inserter device of FIG. 10 according to the preferred embodiment of the invention.

Next, as shown in FIG. 13, the trial inserter device 1000 is used to assist the surgeon in selecting the correct-sized trapezial implant device 110 (shown in FIG. 15) by evaluating the joint height and articulation of trial inserter device 1000 with trapezoid 115, first metacarpal 120, scaphoid 125 and second metacarpal 130 bones. Hole 1305 is then pre-drilled into the base of second metacarpal 130, deep in the trapezial cavity 1205. Also, a hole 1310 is predrilled into first metacarpal 120 above the base, centered palmar to dorsal and angulated towards the volar beak of first metacarpal 120.

Figure 14:
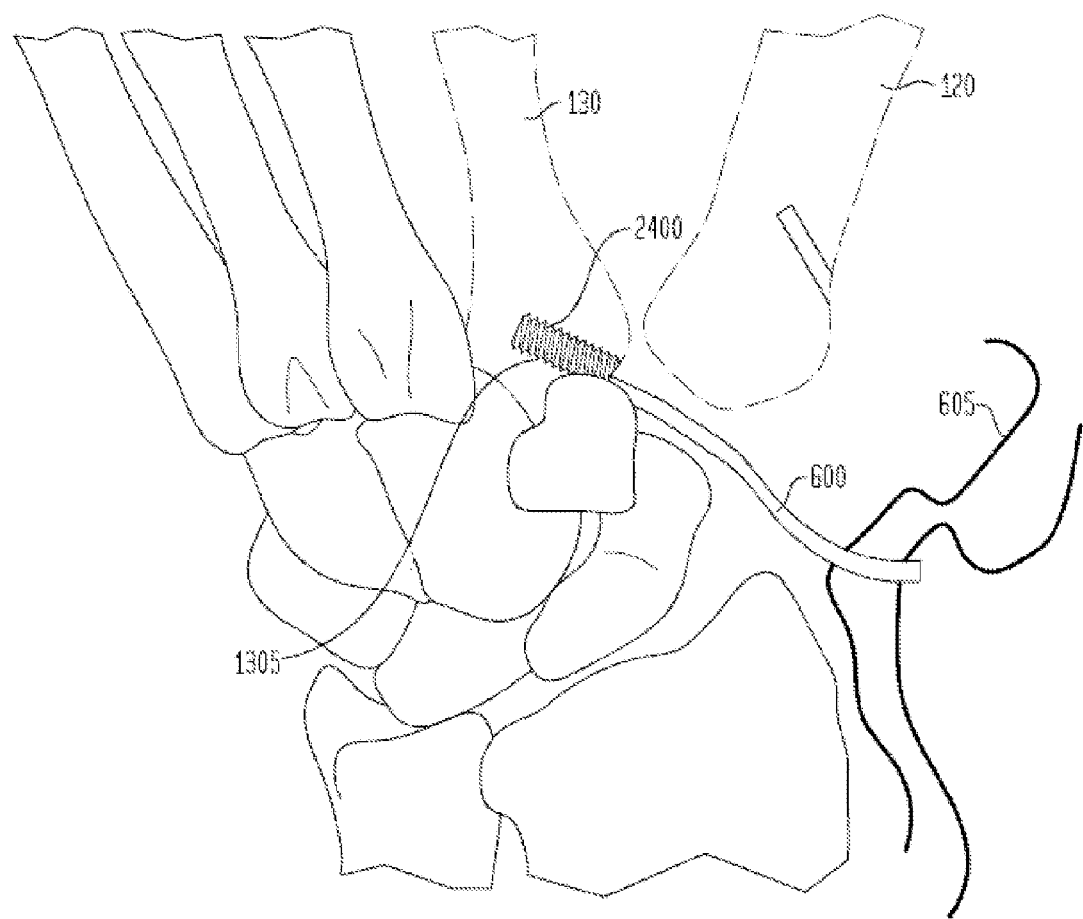
FIG. 14 illustrates a step of attaching a strap to the second metacarpal bone according to the preferred embodiment of the invention.

Next, in the preferred embodiment, and as shown in FIG. 14, after the correct sized trapezial implant device 110 has been selected, the surgeon will insert strap 600 in pre drilled hole 1305, although the holes may also be drilled at this time. Next, an interference screw 2400 is driven into the hole securing the strap 600 in place. Strap 600 is used to attach trapezial implant device 110 to bone in order to reinforce the stability of trapezial implant device 110. The strap contains tails 605. In other non-limiting embodiments, a plurality of substantially similar straps 600 may be utilized to attach trapezial implant device 110 to bones.

Figure 15:
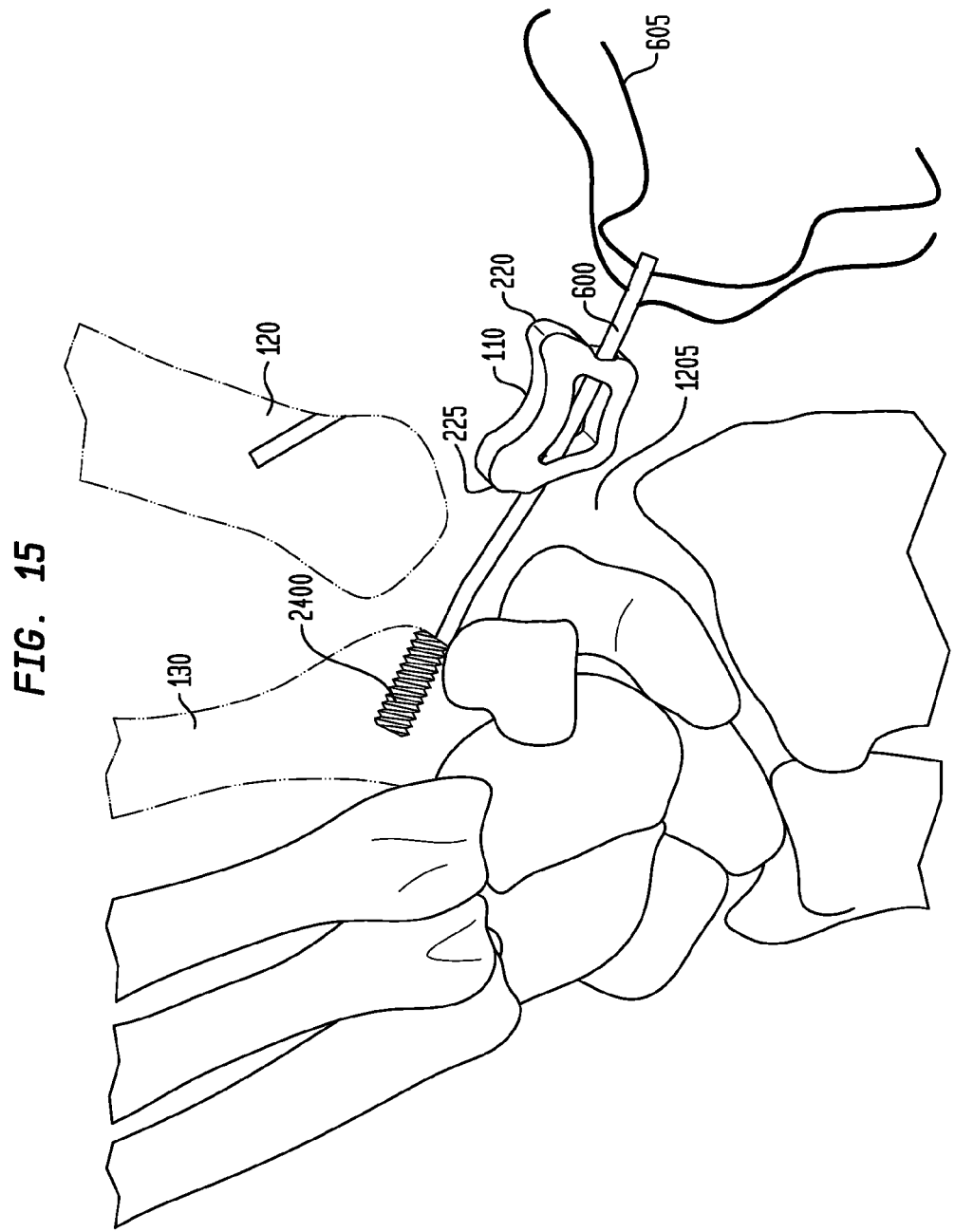
FIG. 15 illustrates a step of inserting a strap into the trapezial implant device of FIG. 2 according to the preferred embodiment of the invention.

Next, as shown in FIG. 15, the surgeon will insert strap 600 through the hole 300 of the trapezial implant device 110 extending from the ulnar face 225 to the radial face 220 (as shown in FIG. 3). The surgeon will then "parachute" or slide the trapezial implant device 110 into the trapezial cavity 1205 using the strap 600.

Figure 16:
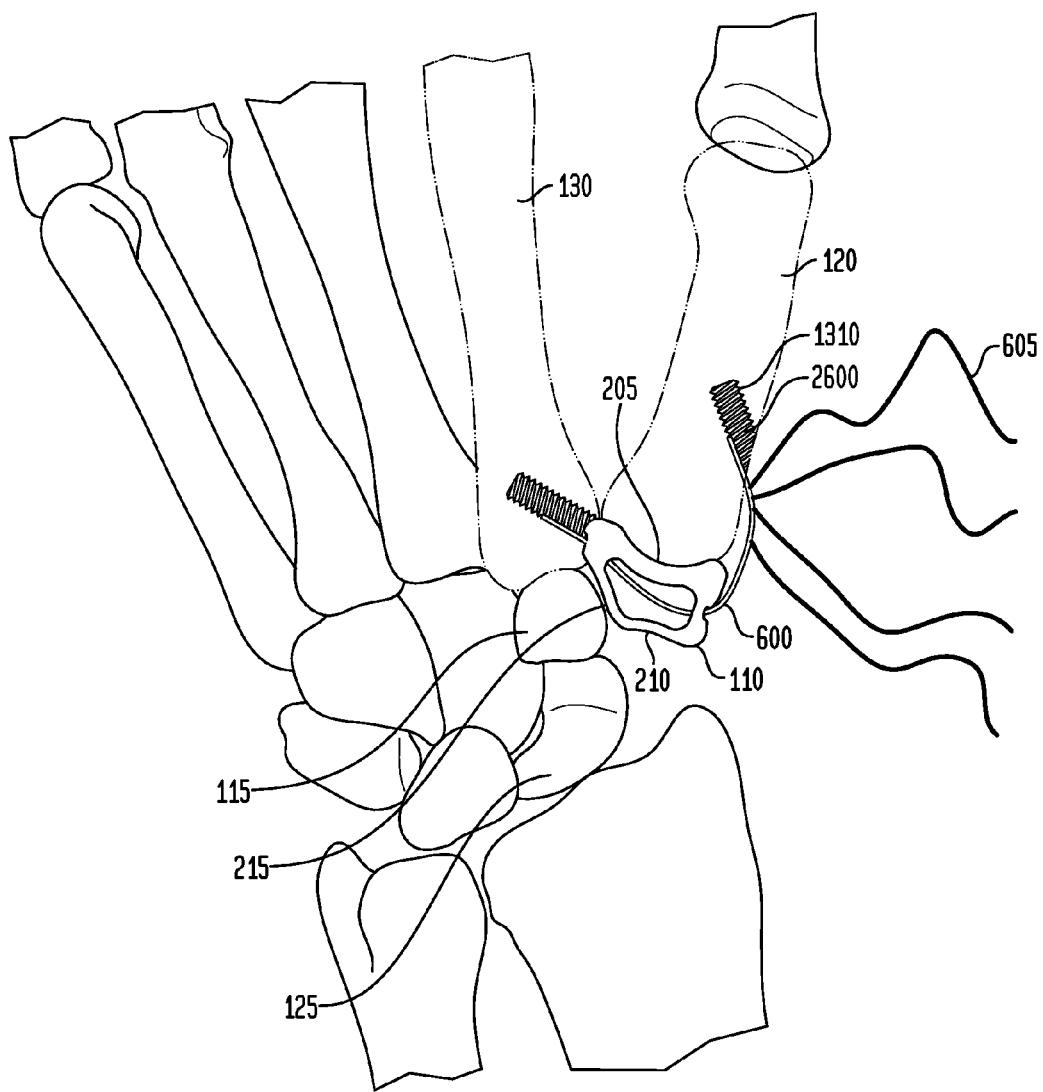
FIG. 16 illustrates a step of attaching a strap to the first metacarpal bone according to the preferred embodiment of the invention.

As shown in FIG. 16, trapezial implant device 110 is preferably positioned so that the first concave surface 205 of implant 110 articulates with the proximal surface of first metacarpal 120 and the second concave surface 210 articulates with the articulating surface of the distal scaphoid 125. Additionally, the third concave surface 215 articulates with the radial articulating surface of the trapezoid bone 115. The fourth surface 225 interfaces with second metacarpal 130.

Next, strap 600 is used to place the trapezial implant device 110 under appropriate tension to first metacarpal 120. The strap 600 is secured by driving an interference screw 2600 into the pre-drilled hole 1310 in the first metacarpal 120 although the holes may also be drilled at this time. Strap 600 now provides a secure "bridge" from the first metacarpal 120 to the second metacarpal 130 to support the trapezial implant device 110. The tails 605 of strap 600 are incorporated in the capsular closure (such as holes 400 and 405 of FIG. 4 and holes 315 and 500 of FIG. 5) to further strengthen and stabilize the carpometacarpal joint and position the trapezial implant device 110. The strap 600 and tails 605 may be further secured to adjacent bones, ligaments, or other tissue to increase the stability of the trapezial implant 110.

Figure 17:
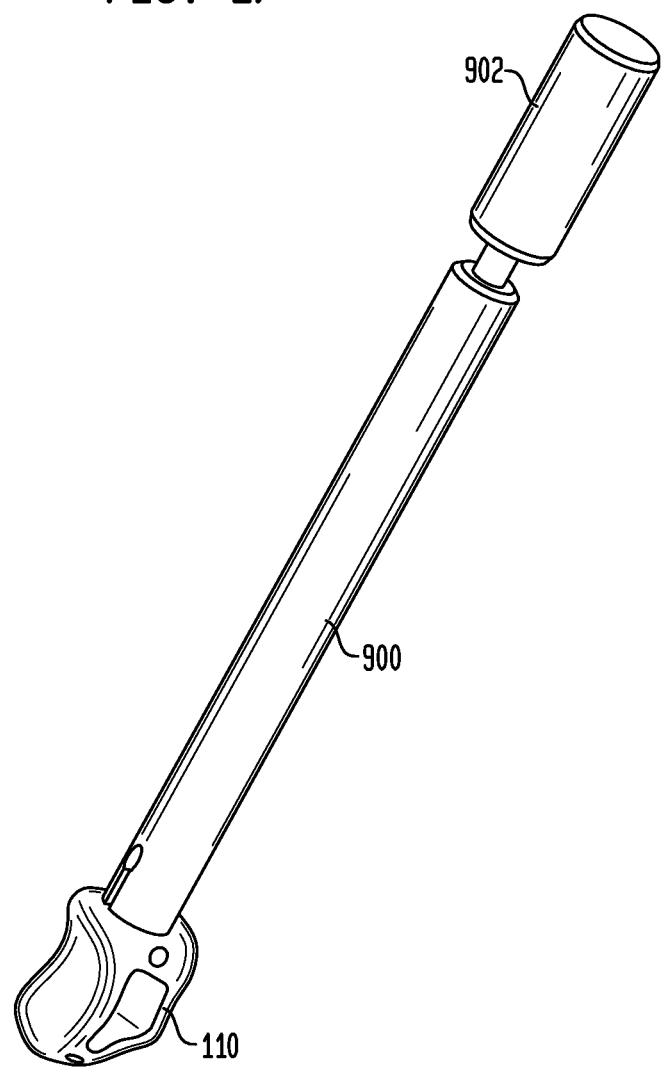
FIG. 17 illustrates a step of inserting the holder instrument of FIG. 9 into the trapezial implant device of FIG. 2 according to the preferred embodiment of the invention.

In another non-limiting embodiment, after the correct sized trapezial implant device 110 has been selected, as shown in FIG. 17, the surgeon will couple holder instrument 900 to trapezial implant device 110 by inserting tip portion 910 (not shown) into aperture 300 (not shown) and rotating handle portion 902 in order to spread tip portion 910 inside aperture 300 and provide an interference fit with trapezial implant device 110.

Figure 18:
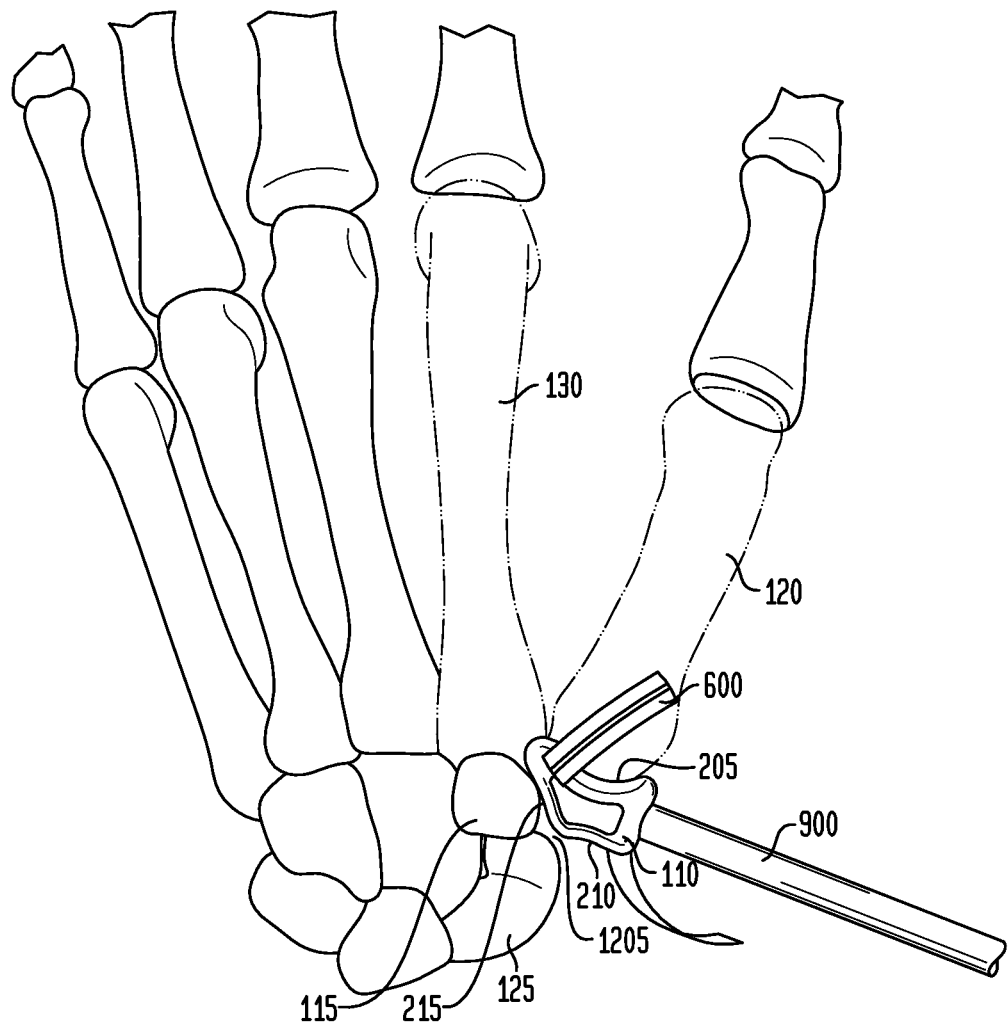
FIG. 18 illustrates a step of attaching the straps of trapezial implant device of FIG. 2 to first metacarpal bone according to an alternate embodiment of the invention.

Next, as shown in FIG. 18 the surgeon will insert strap 600 into through-hole 230 to provide for attaching trapezial implant device 110 to bone in order to reinforce the stability of trapezial implant device 110. In other non-limiting embodiments, a plurality of substantially similar straps 600 may be utilized to attach trapezial implant device 110 to bones.

Next, trapezial implant device 110 is inserted into the trapezial cavity 1205 formed as a result of a trapeziectomy using holder instrument 900. Trapezial implant device 110 is preferably positioned so that the first concave surface 205 of implant 110 articulates with the proximal surface of first metacarpal 120 and the second concave surface 210 articulates with the articulating surface of the distal scaphoid 125. Additionally, the third concave surface 215 articulates with the radial articulating surface of the trapezoid bone 115. The fourth surface 225 interfaces with second metacarpal 130. The handle portion 902 (shown in FIG. 17) of the holder instrument 900 is rotated to remove the interference fit with trapezial implant device 110. Then, the holder instrument 900 is removed from trapezial implant device 110. Also, strap 600 is attached to soft tissue or bone with sutures, although in other non-limiting embodiments, screw fixation, staples, biotenodesis devices, suture anchors or interference screws may be utilized.

Figure 19:
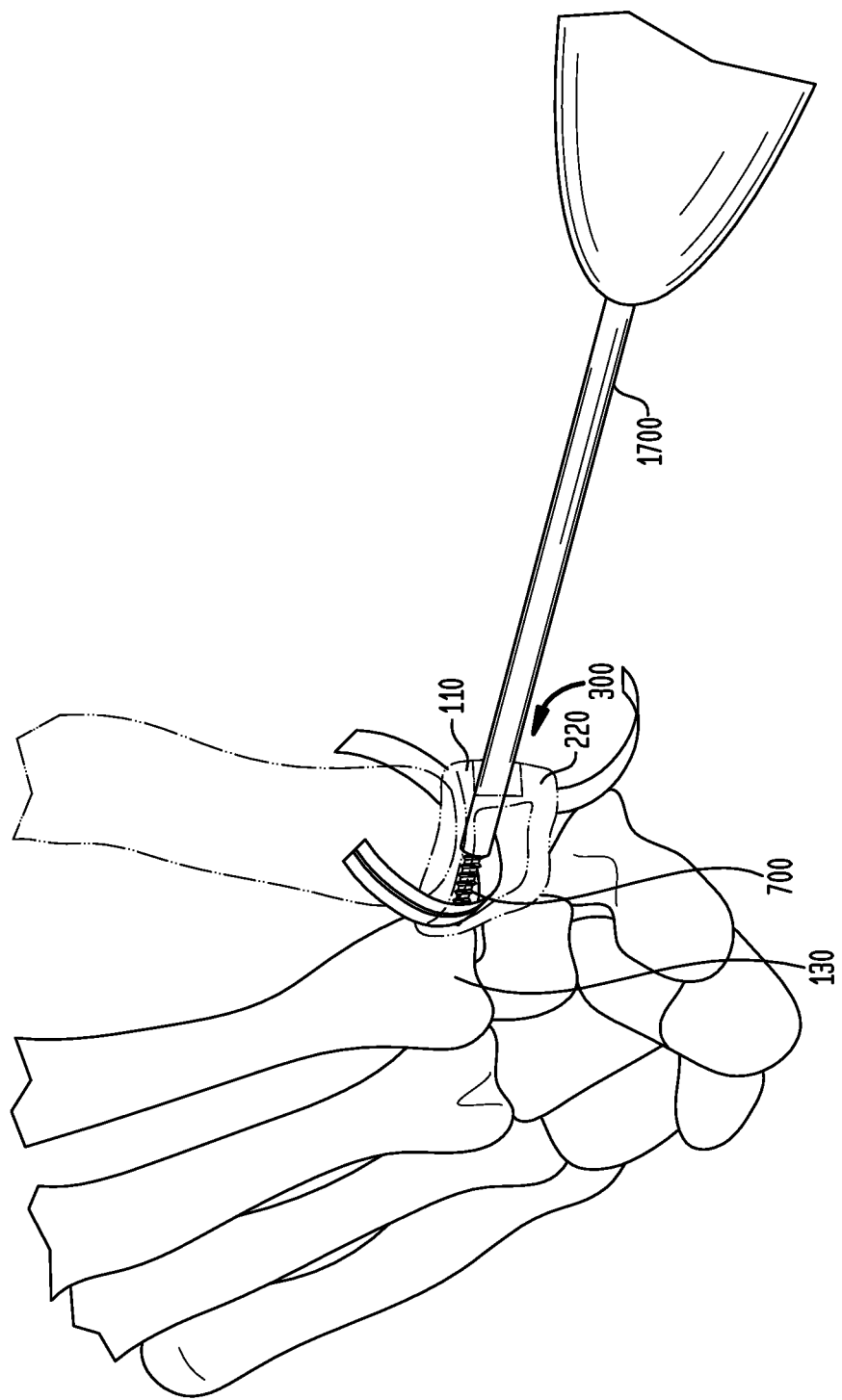
FIG. 19 illustrates a step of installing the trapezial implant device of FIG. 2 using an anchor screw according to an alternate embodiment of the invention.
Figure 20:
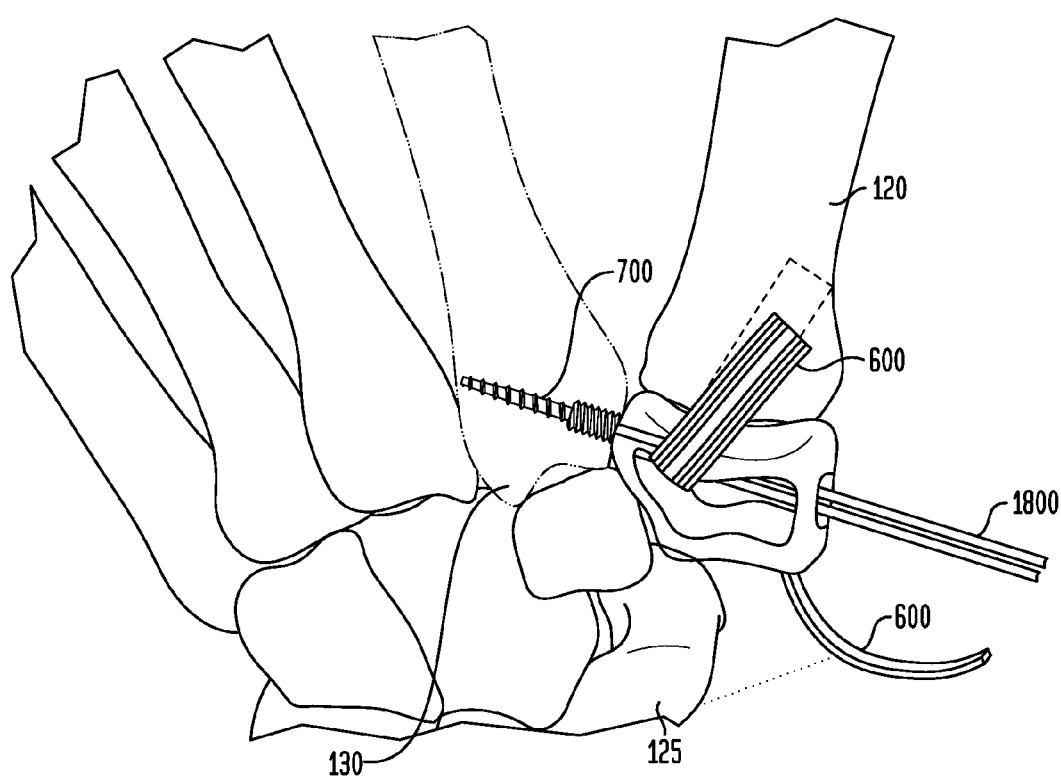
FIG. 20 illustrates a step of installing the trapezial implant device of FIG. 2 using the anchor screw of FIG. 19 according to an alternate embodiment of the invention.

Next, as shown in FIGS. 19 and 20, cancellous threaded screw anchor 700 having, for example, a suture 1800 is inserted into aperture 300 of trapezial implant device 110 at radial face 220. The threaded screw anchor 700 is driven through trapezial implant device 110 and into the pre-drilled hole at the base of second metacarpal 130 through the use of screwdriver 1700. In other non-limiting embodiments, retention tape or a suture is coupled to an interference screw driver and inserted into the pre-drilled hole and secured with the threaded screw anchor 700 and then coupled to trapezial implant device 110.

Next, as shown in FIG. 20, the threaded screw anchor 700 is driven further into second metacarpal 130 so that threaded screw anchor 700 penetrates second metacarpal 130 and causes suture 1800 to penetrate the second metacarpal 130. The remaining suture 1800 is reflected back proximally to secure to trapezial implant device 110 and adjacent tendons and the excess is cut-off. Also, one or more substantially similar straps 600 are attached to soft tissue of the first metacarpal 120 and the scaphoid 125 bones to increase the stability of trapezial implant device 110.

Figure 21:
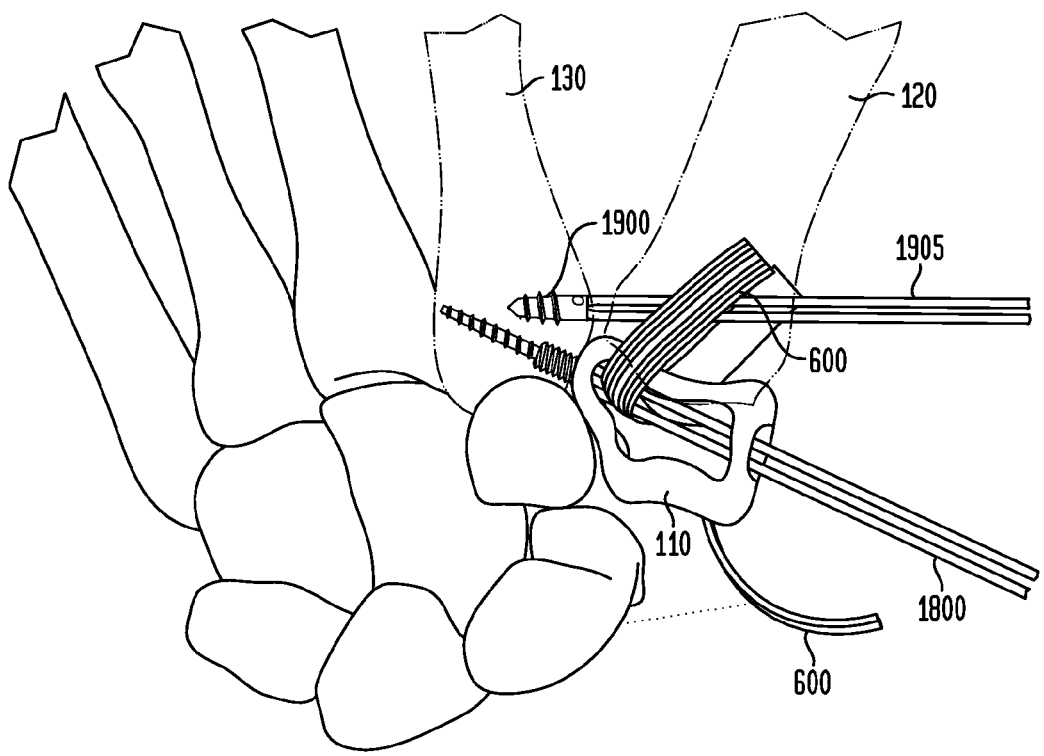
FIG. 21 illustrates a step of installing the trapezial implant device of FIG. 2 using a second anchor screw according to an alternate embodiment of the invention.

As shown in FIG. 21, a second screw anchor 1900 having, for example, a suture 1905 is driven through the pre-drilled hole in first metacarpal 120 and second metacarpal 130 so that threaded screw anchor 1900 traverses through first metacarpal 120 and anchors into second metacarpal 130 causing suture 1905 to traverse first metacarpal 120 and embed inside second metacarpal 130. Next, the stability and motion of first metacarpal 120 is checked. The remaining suture 1905 is reflected back proximally to secure to trapezial implant device 110 and adjacent tendons and the excess is cut-off. The sutures 1800 and 1905 cooperatively with the straps 600 increase the stability of the trapezial implant device 110.

Figure 22:
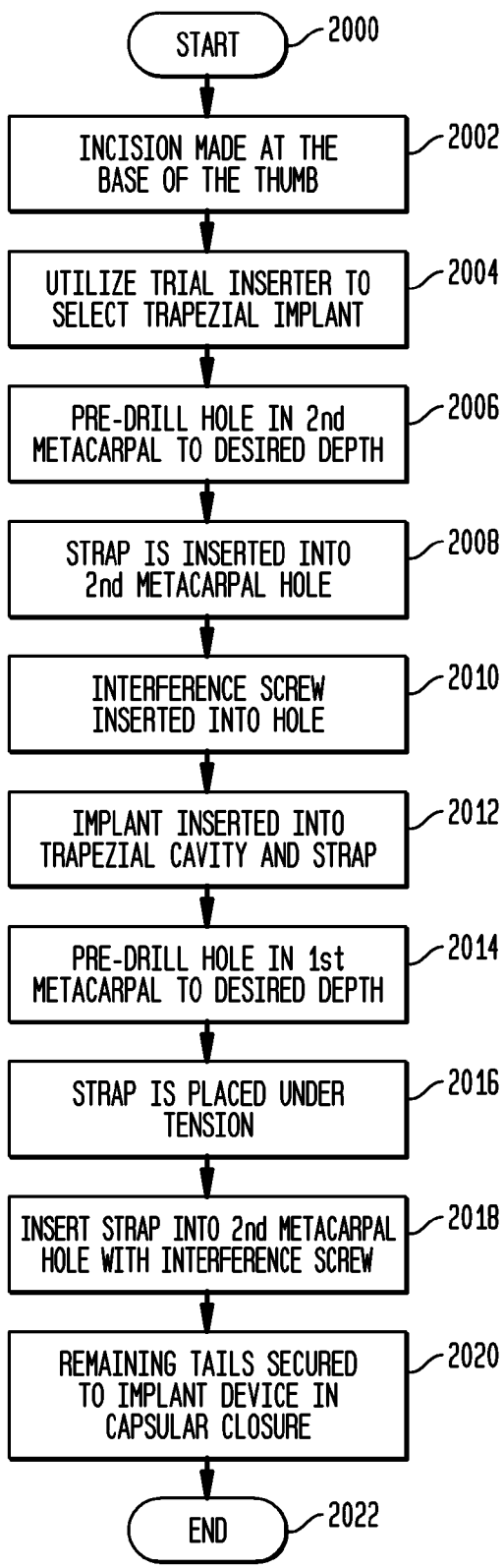
FIG. 22 is a flow chart illustrating the method of inserting the trapezial implant device in the carpometacarpal joint according to the preferred embodiment of the invention.

Referring now to FIG. 22, there is shown a flow chart for utilizing carpometacarpal joint replacement system 100 to replace the trapezium bone with trapezial implant device 110 according to the process shown in FIGS. 14-16. The method starts in step 2000 and proceeds to step 2002, whereby an incision is made in the dorsal-radial longitudinal base of the thumb and a trapeziectomy is performed. Next, in step 2004, trial inserter device is used to assist the surgeon in selecting the correct-sized trapezial implant device and, in step 2006, a hole is pre-drilled into the base of the second metacarpal at a desired depth and location. Next, in step 2008, a strap is inserted into the hole to provide for attaching trapezial implant device to bone. Next in step 2010, an interference screw is inserted into the hole securing the strap in place. In step 2012, trapezial implant device is inserted into the trapezial cavity by "parachuting" or sliding the trapezium prosthesis into the trapezium cavity with the strap in the opening from the ulnar face of the implant to the radial face of the implant. In step 2014, a hole is pre-drilled in the first metacarpal in the desired location at the desired depth. Next, in step 2016, the strap is placed under appropriate tension. Next, in step 2018, the loose end of the strap is secured into the predrilled-hole of the first metacarpal by driving an interference screw into the hole. The strap now provides a secure "bridge" from the first metacarpal to the second metacarpal. Next, in step 2020, the tails of the strap are secured to trapezial implant device in the capsular closure to further strengthen and stabilize the carpometacarpal joint and trapezial implant device position. The method ends in step 2022.

Figure 23:
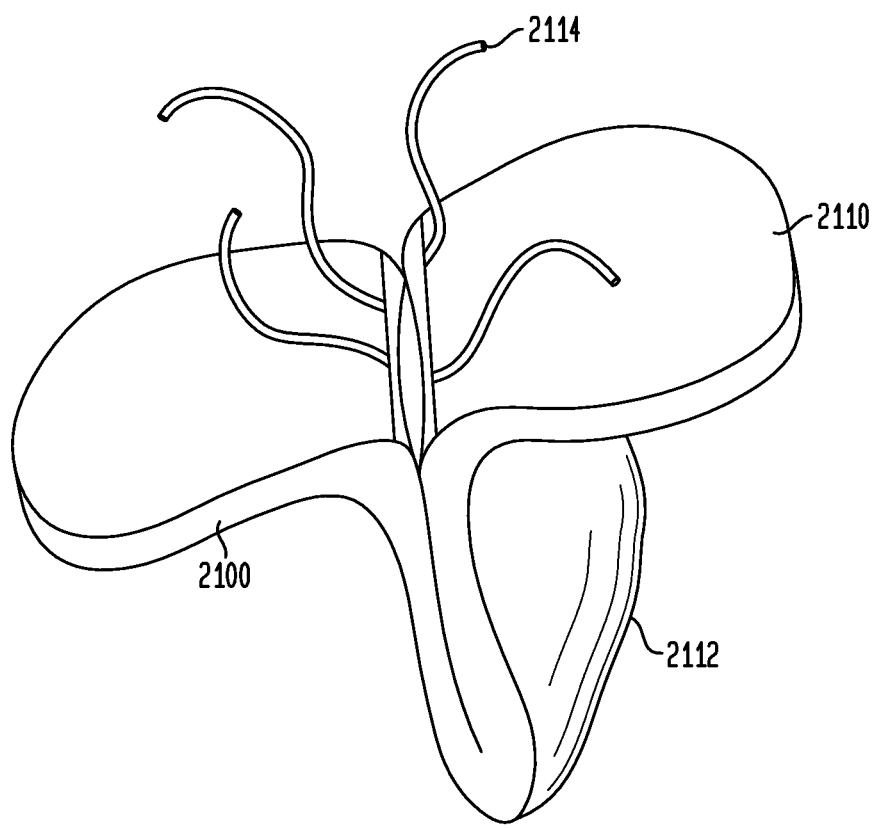
FIG. 23 is a perspective view of a pouch used in the carpometacarpal joint replacement system according to an alternate embodiment of the invention.

As shown in FIG. 23, an implant pouch device 2110 preferably has a non-rigid body 2100 and comprises a shape that fills in the area of the missing trapezium bone. Alternatively, only the deteriorated portion of the trapezium bone is removed and the non-rigid body 2100 only fills the area of the missing trapezium bone portion (not shown). Implant pouch device 2110 has a pouch 2112 and a plurality strings 2114. Strings 2114 are provided to be attached to adjacent bones. Strings 2114 are generally string or ribbon-shaped.

Figure 24:
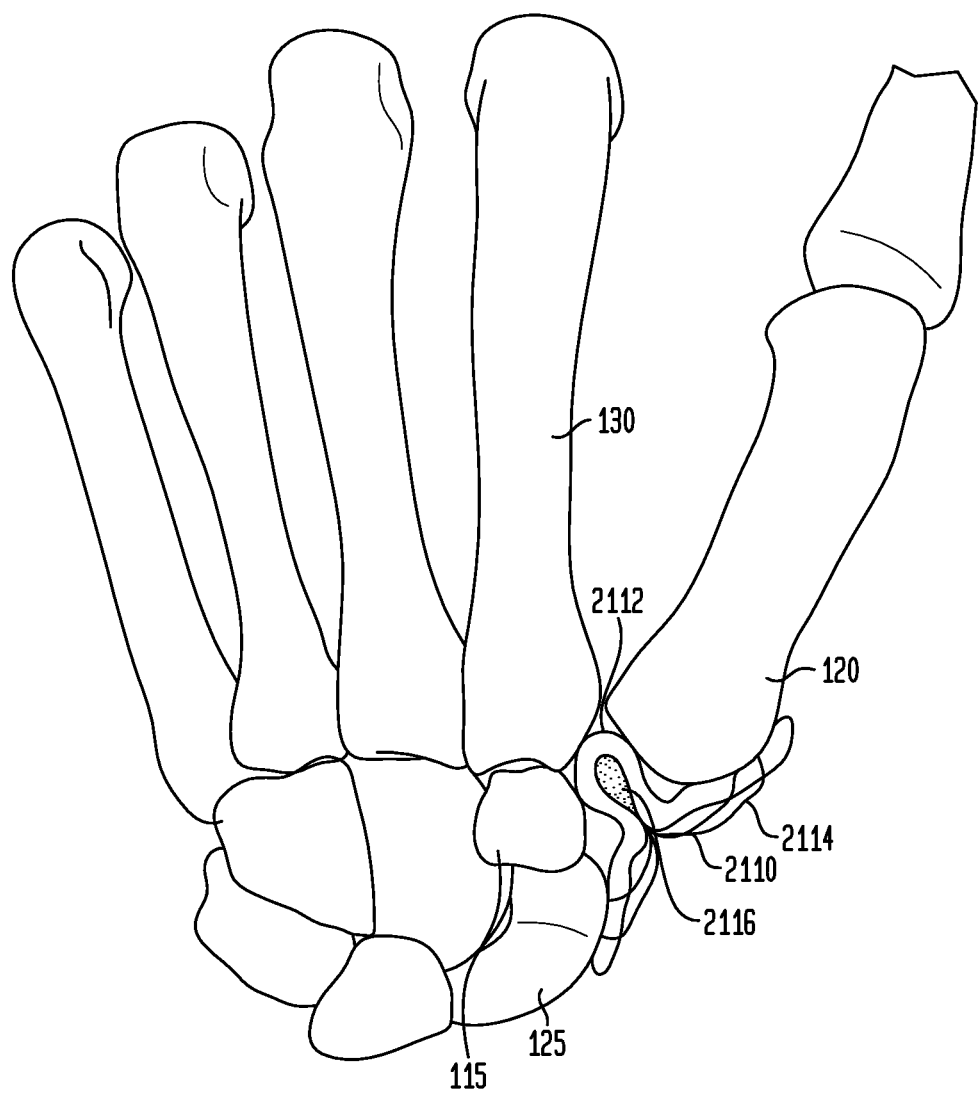
FIG. 24 is a perspective view of the pouch shown in FIG. 23 attached to the carpometacarpal joint according to an embodiment of the invention.

As shown in FIG. 24, implant pouch device 2110 includes a cavity to receive a biologic material 2116 disposed in the pouch 2112. The pouch containing the biologic material 2116 serves as a cushion to prevent bone to bone contact and to prevent the collapse of the adjacent first metacarpal 120, second metacarpal 130, trapezoid 115 and scaphoid 125 bones into the surgically created void (not shown). A tendon, such as the palmaris longus or flexor carpi radialis may be used as the biologic material 2116. The tendon may be harvested from the forearm and rolled up, resembling a rolled "anchovy" or jelly-roll. The tendon is then inserted into the pouch 2112 to prevent unrolling and is interposed between the base of the first metacarpal 120 and the scaphoid 125, the space previously occupied by the trapezium bone (not shown). The implant pouch device 2110 may be attached to adjacent bones, ligaments or other tissue as discussed above using screws, sutures, staples, or the like, thereby increasing the stability of implant pouch device 2110.

It should be understood that this invention is not limited to the disclosed features and other similar method and system may be utilized without departing from the spirit and the scope of the invention.

While the invention has been described with reference to the preferred embodiment and alternative embodiments, which embodiments have been set forth in considerable detail for the purposes of making a complete disclosure of the invention, such embodiments are merely exemplary and are not intended to be limiting or represent an exhaustive enumeration of all aspects of the invention. The scope of the invention, therefore, shall be defined solely by the following claims. Further, it will be apparent to those of skill in the art that numerous changes may be made in such details without departing from the spirit and the principles of the invention. It should be appreciated that the invention is capable of being embodied in other forms without departing from its essential characteristics.

What is claimed is:

1. A prosthetic device for replacing a trapezium in a human hand, the prosthetic device comprising:
   a non-resorbable, rigid body having a curved synthetic body sized and shaped to resemble a trapezium bone in said hand, said rigid body comprising a first articulating concave surface capable of engaging a proximal surface of a first metacarpal bone in said hand, a second articulating concave surface capable of engaging a distal surface of a scaphoid bone in said hand, and a third articulating concave surface capable of engaging a proximal surface of a trapezoid bone in said hand;
   a first through-aperture longitudinally formed in said rigid body, said first through-aperture extends at an angle from an ulnar face to a radial face of said rigid body, wherein said ulnar face comprises an articulating surface capable of engaging a surface of a second metacarpal bone in said hand;
   a fixation device comprising a suture or strap and a threaded screw member to fix said rigid body to said second metacarpal bone, said trapezoid bone, or said first metacarpal bone, wherein said first through aperture receives said suture or strap, and wherein said suture or strap comprises a plurality of tails that weave through a plurality of holes formed in said rigid body; and
   a second through-aperture traversing said rigid body from a dorsal face to a volar face formed to provide a channel for soft tissue growth.

2. The prosthetic device of claim 1, wherein said rigid body is comprised of a material selected from the group consisting of: titanium, stainless steel (SST), polyetheretherketone (PEEK), Cobalt Chrome, polyethylene, polycarbonate, polyurethane, and combinations thereof.

3. The prosthetic device of claim 1, wherein the plurality of holes are formed through the radial face, the ulnar face, or a combination thereof.

4. A prosthetic device for replacing a trapezium in a human hand, the prosthetic device comprising:
   a non-resorbable rigid body sized and shaped to resemble a trapezium bone in said hand, said rigid body comprising a first concave surface capable of engaging a proximal surface of a first metacarpal bone in said hand, a second concave surface capable of engaging a distal surface of a scaphoid bone in said hand, and a third concave surface capable of engaging a proximal surface of a trapezoid bone in said hand;
   a first through-aperture formed in said rigid body, said first through-aperture extending from an ulnar face to a radial face of said rigid body; and
   a fixation device capable of fixing said rigid body to a second metacarpal bone, a trapezoid bone, or the first metacarpal bone, wherein said fixation device comprises a threaded screw member and a strap, wherein said first through aperture receives said strap, and wherein said strap comprises a plurality of tails that weave through a plurality of holes formed in said rigid body.

5. The prosthetic device of claim 4, wherein said rigid body comprises a second through-aperture traversing said rigid body from a fourth surface to a fifth surface of said rigid body.

6. The prosthetic device of claim 5, wherein said second through-aperture is formed to provide a channel for soft tissue growth.

7. The prosthetic device of claim 5, wherein said fourth surface comprises a dorsal face and said fifth surface comprises a volar face of said rigid body.

8. The prosthetic device of claim 4, wherein at least one of said first surface, said second surface, and said third surface comprises an articulating surface capable of engaging at least one bone in said hand.

9. The prosthetic device of claim 4, wherein said ulnar face comprises an articulating surface capable of engaging a surface of said second metacarpal bone in said hand.

10. The prosthetic device of claim 4, wherein said rigid body is comprised of a material selected from the group consisting of: titanium, stainless steel (SST), polyetheretherketone (PEEK), Cobalt Chrome, polyethylene, polycarbonate, polyurethane, and combinations thereof.

11. The prosthetic device of claim 4, wherein said threaded screw member is capable of being affixed to a hole formed in the second metacarpal bone or the first metacarpal bone.

12. The prosthetic device of claim 4, wherein the plurality of holes are formed through the radial face, the ulnar face, or a combination thereof.

13. The prosthetic device of claim 4 wherein the first surface extends from the radial face to the ulnar face, wherein the second surface extends from the radial face to the third surface, and wherein the third surface extends from the ulnar face to the second surface.

14. The prosthetic device of claim 4 wherein the first through-aperture extends at an angle from the ulnar face to the radial face of said rigid body.

15. A prosthetic device for replacing a trapezium in a human hand, the prosthetic device comprising:
   a non-resorbable rigid body having a first concave surface capable of engaging a proximal surface of a first metacarpal bone in said hand, a second concave surface capable of engaging a distal surface of a scaphoid bone in said hand, and a third concave surface capable of engaging a proximal surface of a trapezoid bone in said hand;

a first through-aperture formed in said rigid body, wherein said first through-aperture extends from an ulnar face to a radial face of said rigid body;

a suture or strap to fix said rigid body to a second metacarpal bone, a trapezoid bone, or said first metacarpal bone, wherein said first through aperture receives said suture or strap, and wherein said suture or strap comprises a plurality of tails that weave through a plurality of holes formed in said rigid body; and a second through-aperture formed in said rigid body to provide a channel for soft tissue growth, wherein said second through-aperture extends from a dorsal face to a volar face of said rigid body.

16. The prosthetic device of claim 15, wherein said suture or strap is coupled to a threaded screw.

17. The prosthetic device of claim 15, wherein the plurality of holes are formed through the radial face, the ulnar face, or a combination thereof.

18. A prosthetic device for replacing a trapezium in a human hand, the prosthetic device comprising:

a non-resorbable, rigid body having a curved synthetic body sized and shaped to resemble a trapezium bone in said hand, said rigid body comprising a first concave surface capable of engaging a surface of a first metacarpal bone in said hand, a second concave surface capable of engaging a surface of a scaphoid bone in said hand, and a third concave surface capable of engaging a surface of a trapezoid bone in said hand;

a first through-aperture longitudinally formed in said rigid body, said first through-aperture extending at an angle from an ulnar face to a radial face of said rigid body;

a suture or strap to fix said rigid body to a second metacarpal bone, said trapezoid bone, or said first metacarpal bone, wherein said first through aperture receives said suture or strap, and wherein said suture or strap comprises a plurality of tails that weave through a plurality of holes formed in said rigid body; and a second through-aperture traversing said rigid body from a dorsal face to a volar face formed to provide a channel for soft tissue growth.

19. The prosthetic device of claim 18, wherein said suture or strap is coupled to a threaded screw.

20. The prosthetic device of claim 18, wherein the plurality of holes are formed through the radial face, the ulnar face, or a combination thereof.

* * * * *